United States Patent
Smith

(10) Patent No.: US 9,084,633 B2
(45) Date of Patent: *Jul. 21, 2015

(54) PEDICLE SCREW

(71) Applicant: J. Scott Smith, Granbury, TX (US)

(72) Inventor: J. Scott Smith, Granbury, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/256,742

(22) Filed: Apr. 18, 2014

(65) Prior Publication Data

US 2014/0214099 A1    Jul. 31, 2014

Related U.S. Application Data

(63) Continuation of application No. 12/132,476, filed on Jun. 3, 2008, now Pat. No. 8,740,956.

(60) Provisional application No. 61/010,669, filed on Jan. 10, 2008.

(51) Int. Cl.
| | |
|---|---|
| A61B 17/70 | (2006.01) |
| A61B 17/84 | (2006.01) |
| A61B 17/86 | (2006.01) |
| A61B 17/58 | (2006.01) |
| A61B 19/00 | (2006.01) |

(52) U.S. Cl.
CPC ........... *A61B 17/7032* (2013.01); *A61B 17/58* (2013.01); *A61B 17/84* (2013.01); *A61B 17/863* (2013.01); *A61B 17/8605* (2013.01); *A61B 17/8625* (2013.01); *A61B 2019/5437* (2013.01)

(58) Field of Classification Search
USPC .................................................. 606/314–316
See application file for complete search history.

(56) References Cited

U.S. PATENT DOCUMENTS

| | | |
|---|---|---|
| 3,499,222 A | 3/1970 | Edelman et al. |
| 4,537,185 A | 8/1985 | Stednitz |
| 4,858,601 A | 8/1989 | Glisson |
| 5,019,079 A | 5/1991 | Ross |
| 5,324,199 A | 6/1994 | Brånemark |
| 5,769,852 A * | 6/1998 | Brånemark ............ 606/65 |
| 5,989,025 A | 11/1999 | Conly |
| 6,015,937 A * | 1/2000 | Brånemark ............ 606/65 |
| 6,033,438 A | 3/2000 | Bianchi et al. |
| 6,053,916 A | 4/2000 | Moore |
| 6,174,330 B1 | 1/2001 | Stinson |
| 6,224,598 B1 | 5/2001 | Jackson |
| 6,248,105 B1 | 6/2001 | Schlapfer |
| 6,280,442 B1 | 8/2001 | Barker |
| 6,302,888 B1 | 10/2001 | Mellinger |
| 6,440,137 B1 | 8/2002 | Horvath |
| 6,443,953 B1 | 9/2002 | Perra |
| 6,565,567 B1 | 5/2003 | Haider |
| 6,755,829 B1 | 6/2004 | Bono |
| 6,921,403 B2 | 7/2005 | Cragg et al. |
| 7,186,255 B2 | 3/2007 | Baynam |

(Continued)

OTHER PUBLICATIONS

U.S. Appl. No. 12/132,476, filed Jun. 30, 2008, J. Scott Smith.

(Continued)

*Primary Examiner* — Christian Sevilla
(74) *Attorney, Agent, or Firm* — Workman Nydegger

(57) ABSTRACT

A screw, comprising a head, and a shaft, wherein the shaft comprised a first threaded shaft portion; a second threaded shaft portion disposed contiguous to said head; and a middle shaft portion disposed between said first threaded shaft portion and said second threaded shaft, wherein said middle shaft portion is an irregular form.

10 Claims, 2 Drawing Sheets

(56) References Cited

U.S. PATENT DOCUMENTS

| | | |
|---|---|---|
| 7,235,076 B2 | 6/2007 | Pacheco |
| 7,261,716 B2 * | 8/2007 | Strobel et al. ............... 606/314 |
| 7,294,128 B2 | 11/2007 | Alleyne |
| 7,691,129 B2 | 4/2010 | Felix |
| 7,871,413 B2 | 1/2011 | Park |
| 7,967,850 B2 | 6/2011 | Jackson |
| 8,016,862 B2 | 9/2011 | Felix et al. |
| 8,016,866 B2 | 9/2011 | Warnick |
| 8,197,517 B1 | 6/2012 | Lab et al. |
| 8,740,956 B2 * | 6/2014 | Smith ..................... 606/315 |
| 8,845,693 B2 | 9/2014 | Smith et al. |
| 2002/0038123 A1 | 3/2002 | Visotsky et al. |
| 2004/0220567 A1 | 11/2004 | Eisermann et al. |
| 2004/0220575 A1 * | 11/2004 | Biedermann et al. ........ 606/73 |
| 2005/0113929 A1 | 5/2005 | Cragg et al. |
| 2005/0203523 A1 | 9/2005 | Wenstrom et al. |
| 2005/0261695 A1 | 11/2005 | Cragg et al. |
| 2005/0277918 A1 | 12/2005 | Shah et al. |
| 2006/0089644 A1 | 4/2006 | Felix |
| 2006/0271196 A1 | 11/2006 | Saal et al. |
| 2006/0276788 A1 * | 12/2006 | Berry et al. ................. 606/61 |
| 2007/0055232 A1 | 3/2007 | Colquhoun |
| 2007/0288004 A1 | 12/2007 | Alvarez |
| 2008/0287959 A1 | 11/2008 | Quest et al. |
| 2009/0036934 A1 | 2/2009 | Biedermann |
| 2009/0198280 A1 | 8/2009 | Spratt |
| 2011/0125265 A1 | 5/2011 | Bagga et al. |
| 2014/0148853 A1 | 5/2014 | Smith |
| 2014/0171955 A1 | 6/2014 | Smith |

OTHER PUBLICATIONS

U.S. Appl. No. 13/427,865, filed Mar. 22, 2012, Jeffrey Scott Smith.
U.S. Appl. No. 13/427,841, filed Mar. 22, 2012, Jeffrey Scott Smith.
U.S. Appl. No. 12/132,476, Jan. 18, 2011, Office Action.
U.S. Appl. No. 12/132,476, Jun. 22, 2011, Final Office Action.
U.S. Appl. No. 12/132,476, Sep. 24, 2013, Office Action.
U.S. Appl. No. 12/132,476, Jan. 24, 2014, Notice of Allowance.
U.S. Appl. No. 13/427,865, May 30, 2014, Restriction Requirement.
U.S. Appl. No. 13/427,841, May 30, 2014, Restriction Requirement.
U.S. Appl. No. 13/427,841, Jun. 17, 2014, Office Action.
U.S. Appl. No. 14/591,747, Jan. 7, 2015, Jeffrey Scott Smith.
U.S. Appl. No. 13/427,841, Mar. 4, 2015, Office Action.
U.S. Appl. No. 13/401,339, Aug. 9, 2013, Office Action.
U.S. Appl. No. 13/401,339, Dec. 20, 2013, Final Office Action.
U.S. Appl. No. 13/401,339, Apr. 23, 2014, Advisory Action.
U.S. Appl. No. 13/401,339, May 16, 2014, Notice of Allowance.
U.S. Appl. No. 13/427,841, Sep. 25, 2014, Final Office Action.
U.S. Appl. No. 13/427,865, Nov. 3, 2014, Notice of Allowance.
U.S. Appl. No. 13/427,865, Dec. 5, 2014, Supplemental Notice of Allowance.

* cited by examiner

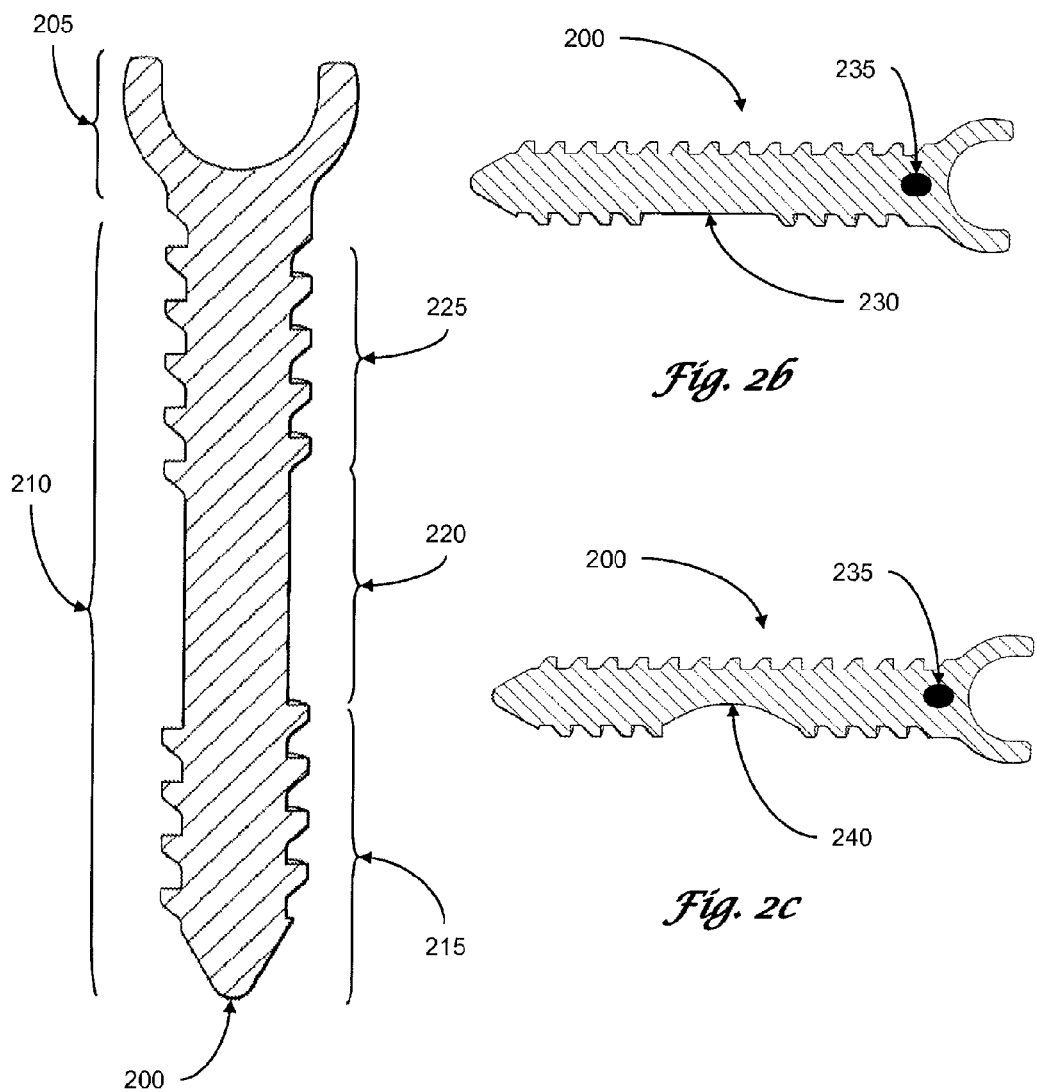

US 9,084,633 B2

PEDICLE SCREW

CROSS-REFERENCE TO RELATED APPLICATIONS

This application is a continuation of and claims benefit of and priority to U.S. patent application Ser. No. 12/132,476 filed on Jun. 3, 2008 and entitled "PEDICLE SCREW," which claims the benefit of and priority to U.S. Provisional Patent Application Ser. No. 61/010,669, filed Jan. 10, 2008, which applications are hereby expressly incorporated herein in their entirety

BACKGROUND OF THE INVENTION

1. The Field of the Invention

The presently preferred embodiment of the innovations described herein relates generally to bone screws. More specifically, the presently preferred embodiment relates to a pedicle screw.

2. The Relevant Technology

The human spine extends from the head to the tailbone, and made-up of bones known as vertebrae. The spine is one of the most important structures in the human body. It is strong but flexible, allowing a wide range of movements. Because the spine is so important for support and movement, a problem, e.g. back disorders, can disrupt even the simplest activities of life. Depending on the condition of the spine, a doctor may choose to use a posterior approach to treat the back disorder that includes the use of a pedicle screw system where a biocompatible screw commonly made of titanium is placed in the pedicle of the vertebrae to provide a base for a further support structure, for example Unfortunately, pedicle screws are not without their inherent problems. Complications from the use of pedicle screws are common, which include loosening, breakage, damage to nearby joints, penetration of major blood vessels, and injuries to delicate neurological structures including nerve roots and the spinal cord. Of these complications, damage to the adjacent neurological structures is among the most debilitating, and difficult to manage. Technology has been introduced over the years in an attempt to decrease the risk of nerve damage associated with placement of pedicle screws, for example, U.S. Pat. No. 7,235,076, titled METHOD OF IMPROVING PEDICLE SCREW PLACEMENT IN SPINAL SURGERY issued Jun. 26, 2007, which describes the use of a determining size and trajectory of a pedicle screw through 3D imaging. The use of intraoperative fluoroscopy can reduce the incidence of misplaced screws, as can technology which utilizes computer guidance-based on preoperative CT scanning. Even with these techniques, the risk of injury to nerve roots from the use of pedicle screw fixation continues to plague the use of these devices.

Nerve root injuries can be devastating. Patients with nerves that have been damaged by poorly placed pedicle screws may fail to recover; leading to chronic and disabling pain. These patients have few treatment options, and often remain in pain for years, if not for their entire lives. The nerve roots may be injured either at the time of surgery, or injury may accumulate over time from the threads of the screws acting against the roots.

What is needed is a new and simple design for a pedicle screw that will greatly reduce, or eliminate, the damage to nerve roots when used by properly trained and qualified surgeons.

BRIEF SUMMARY OF THE INVENTION

To achieve the foregoing, and in accordance with the purpose of the presently preferred embodiment as broadly described herein, the present application provides a screw, comprising a head, and a shaft. The shaft comprising a first threaded shaft portion; a second threaded shaft portion disposed contiguous to said head; and a middle shaft portion disposed between said first threaded shaft portion and said second threaded shaft, wherein said middle shaft portion is an irregular form. The screw, wherein said irregular form is unthreaded. The screw, wherein said irregular form is threaded along half of a middle shaft surface. The screw, wherein said irregular form has a concave feature. The screw, wherein said screw is biocompatible. The screw, wherein said screw is placed in a pedicle.

Another advantage of the presently preferred embodiment is to provide a pedicle screw, comprising a head, and a shaft. The shaft comprising a first threaded shaft portion; a second threaded shaft portion disposed contiguous to said head; and a middle shaft portion disposed between said first threaded shaft portion and said second threaded shaft, wherein said middle shaft portion is one of unthreaded, threaded along half of a middle shaft surface, and has a concave feature.

And another advantage of the presently preferred embodiment is to provide a system for an installed pedicle screw, comprising a drill bit inserted into a pedicle for a predetermined distance to create a pedicle screw cavity, wherein the drill bit is a shaft diameter; a pedicle screw inserted into said pedicle screw cavity, wherein said pedicle screw comprises a head, and a shaft. The shaft comprises a first threaded shaft portion; a second threaded shaft portion disposed contiguous to said head; and a middle shaft portion disposed between said first threaded shaft portion and said second threaded shaft, wherein said middle shaft portion is an irregular form; whereby said installed pedicle screw touches a nerve root. The pedicle screw, wherein said irregular form is unthreaded. The pedicle screw, wherein said irregular form is threaded along half of a surface of said middle shaft. The pedicle screw, wherein said irregular form has a concave feature.

Other advantages of the presently preferred embodiment will be set forth in part in the description and in the drawings that follow, and, in part will be learned by practice of the presently preferred embodiment. The presently preferred embodiment will now be described with reference made to the following Figures that form a part hereof. It is understood that other embodiments may be utilized and changes may be made without departing from the scope of the presently preferred embodiment.

BRIEF DESCRIPTION OF THE DRAWINGS

A presently preferred embodiment will hereinafter be described in conjunction with the appended drawings, wherein like designations denote like elements, and:

FIGS. 2a-2c illustrate a cross-sectional view of a pedicle screw in various embodiments.

DETAILED DESCRIPTION OF THE PREFERRED EMBODIMENTS

Figure 1:
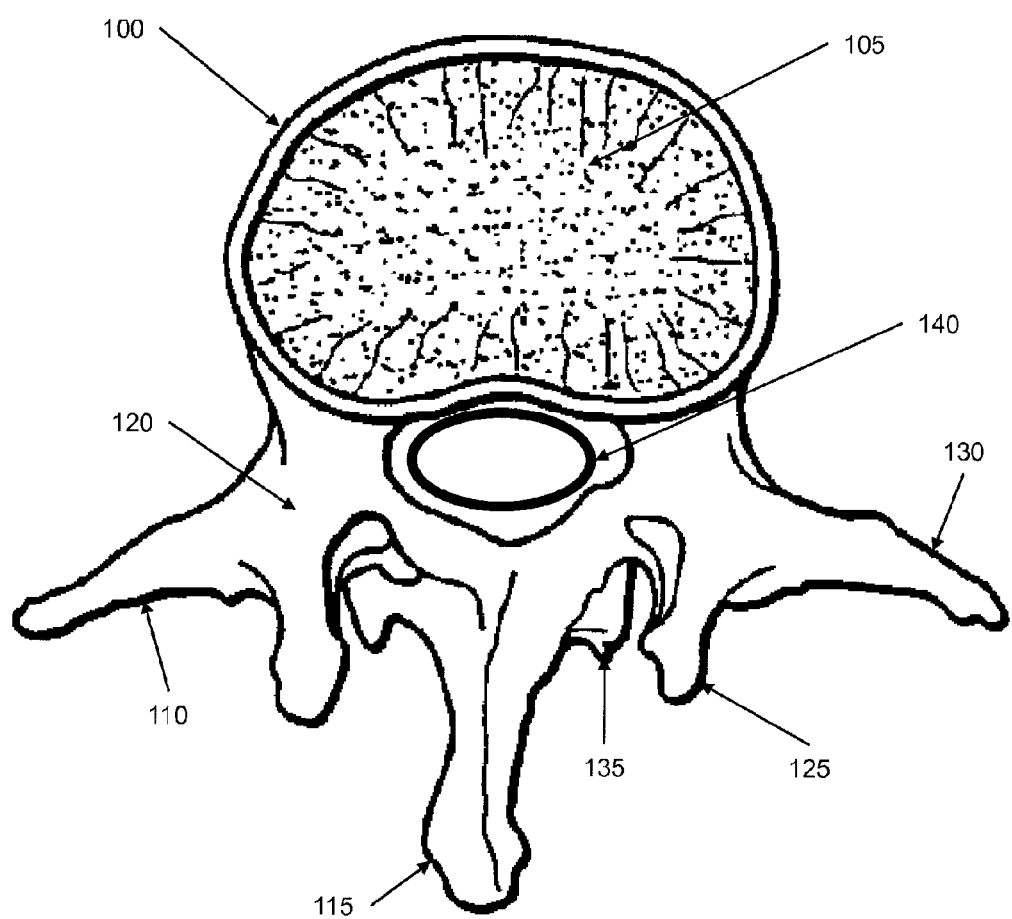
FIG. 1 is an illustration of a vertebra in transverse cross-section.

FIG. 1 is an illustration of a vertebra in transverse cross-section. Referring further to FIG. 1, a typical vertebra 100, is one of the bones comprising a human spine. The vertebra 100 has seven components, a vertebral body 105, a vertebral foramen 110, a spinous process 115, a pedicle 120, a superior articular process 125, a transverse process 130, and a lamina 135. Two vertebral bodies combine to create the vertebral foramen 110 through which passes a nerve root and a spinal cord 140. The human spine various widely across the population, and, accordingly, so does the pedicle 120. Because the pedicle 120 varies in its anatomy, biocompatible hardware must also be available in various shapes and sizes that is inserted into or otherwise affixed to the pedicle 120, for example a bone screw.

FIGS. 2a-2c illustrate a cross-sectional view of a pedicle screw in various embodiments. Referring further to FIG. 2a, the bone screw, e.g., a pedicle screw 200, has a head 205 and a shaft 210. And like any screw, the pedicle screw 200, has various characteristics, for example, a length, a major diameter, a minor diameter, a thread pitch, and a taper profile, that can all be adjusted given the various pedicle pathologies. The shaft 210, for example, can have a major diameter of 6.5 mm, a length of 40 mm, and a thread pitch of 3.0 mm, with other measurements contemplated so that the pedicle screw 200 performs as intended. The pedicle screw 200 has a first threaded shaft portion 215; a middle shaft portion 220; and a second threaded shaft portion 225. The second threaded shaft portion 225 is contiguous to the head 205, but alternatively there can be a shank or other portion disposed between the second threaded shaft portion 225 and the head 205. The middle shaft portion 220 is of an irregular form, which is to say, it does not share at least one of the same characteristics as the first threaded shaft portion 215 and the second threaded shaft portion 225. The pedicle screw 200 preferably has a major/minor diameter combination of cylindrical, so that the middle shaft portion 220 lacks any of the threading in the first and second threaded shaft portions 215, 225, respectively, and is of the cylindrical minor diameter. Any combination of cylindrical and tapered diameters are contemplated within this application, for example, the minor diameter may be tapered and the major diameter cylindrical, in which case, the middle shaft portion 220 would have the tapered minor diameter. Other embodiments of the presently preferred embodiment are also contemplated, for example, those described below.

Referring further to FIGS. 2b and 2c, the middle shaft portion 220 can be threaded along a portion, or, for example, half, of its cylindrical (or tapered) surface, generally shown at 230. In this embodiment a marker 235 is placed on the head 105 as a visual indicator of the location of the non-threaded minor diameter of the middle shaft portion 220. The marker 305 allows for the proper alignment of the pedicle screw 200 such that the threads of the middle shaft portion are to minimize potential thread contact with the nerve root or spinal chord 140. Referring to FIG. 2c, the middle shaft portion 220 has a concave feature 240, for example. The concave feature 240 can be threaded, and is preferably threaded on the non-concave portion, so that when inserted into the pedicle 120, the pedicle screw 200 is aligned such that the concave feature 240 minimizes contact with the associated nerve root.

In practice, when pedicle screws are evenly placed with the assistance or the aid of intra-operative fluoroscopy and/or CT guided imaging techniques, for example, there still exists the possibility of placement error that can go undetected resulting in nerve root damage and/or injury. Therefore, it is contemplated that the placement of the pedicle screw 200 directly addresses when these drilling errors are known so that the disclosed pedicle screw 200 will greatly lesson damage caused by the threads of prior-art pedicle screws.

A number of embodiments have been described. It will be understood that various modifications may be made without departing from the spirit and scope of the presently preferred embodiment. For example, the biocompatible material contemplated is titanium, but other biocompatible materials are also applicable. The middle shaft portion 220 can be fully threaded but with a smaller thread diameter, or with blunt edges to protect the nerve. Further, the middle shaft portion 220 can be rotated to turn threads away from the foramin or away form the medial wall of the pedicle. Also, the head 205 can be rotatable for easy positioning and manipulation. Therefore, other implementations are within the scope of the following claims.

What is claimed is:

1. A pedicle screw comprising:
   a head portion providing a base for attachment of a supporting structure for the spine, comprising;
   a shaft comprising:
   a first threaded shaft portion;
   a second threaded shaft portion disposed contiguous to said head; and
   a middle shaft portion disposed between said first threaded shaft portion and said second threaded shaft portion;
   wherein said middle shaft portion has a partial non-threaded shaft portion and has a partial threaded shaft portion in which threads of said partial threaded shaft portion extend circumferentially along a longitudinal side portion of said middle shaft portion and wherein said partial threaded shaft portion is on an opposite side of said shaft from said partial non-threaded shaft portion;
   and further wherein said pedicle screw is a unitary structure, and further wherein at least one of said threaded shaft portions is threaded substantially the entire circumference of said shaft.

2. The pedicle screw of claim 1 wherein said head portion contains means to visually indicate the location of the unthreaded shaft portion when installed in a pedicle.

3. The pedicle screw of claim 1 wherein the portion of said partial threaded portion of the shaft that is threaded is about one-half.

4. A process for installing a pedicle screw into a spinal structure using a guided imaging technique, whereby the pedicle screw is the pedicle screw of claim 1.

5. The pedicle screw of claim 1 wherein the partial non-threaded shaft portion of said middle portion of said screw is concave in configuration.

6. A system for supporting a spine comprising at least one pedicle screw as defined in claim 1.

7. The system of claim 6, wherein said pedicle screw contains means to visually indicate the location of the unthreaded shaft portion when installed in a pedicle.

8. The system of claim 6, wherein the portion of said partial threaded portion of the shaft that is threaded is about one-half.

9. The system of claim 6, whereby said partial non-threaded shaft portion of said pedicle screw does not irritate a nerve root.

10. The pedicle screw system of claim 6 wherein the partial non-threaded shaft portion of said middle portion of said screw is concave in configuration.

* * * * *